(12) United States Patent
Zhang et al.

(10) Patent No.: US 11,667,901 B2
(45) Date of Patent: Jun. 6, 2023

(54) CHONDROSULPHATASE AND USE THEREOF

(71) Applicant: NANJING HANXIN PHARMACEUTICAL INC, Jiangsu (CN)

(72) Inventors: Haoning Zhang, Jiangsu (CN); Song Chen, Jiangsu (CN); Chuangen Tang, Jiangsu (CN); Jing Wang, Jiangsu (CN)

(73) Assignee: NANJING HANXIN PHARMACEUTICAL INC, Jiangsu (CN)

( * ) Notice: Subject to any disclaimer, the term of this patent is extended or adjusted under 35 U.S.C. 154(b) by 0 days.

(21) Appl. No.: 17/601,080

(22) PCT Filed: Sep. 18, 2019

(86) PCT No.: PCT/CN2019/106448
§ 371 (c)(1),
(2) Date: Oct. 3, 2021

(87) PCT Pub. No.: WO2020/199521
PCT Pub. Date: Oct. 8, 2020

(65) Prior Publication Data
US 2022/0259577 A1    Aug. 18, 2022

(30) Foreign Application Priority Data
Apr. 3, 2019 (CN) .......................... 201910264385.5

(51) Int. Cl.
*C12N 9/16* (2006.01)

(52) U.S. Cl.
CPC ........ *C12N 9/16* (2013.01); *C12Y 301/06004* (2013.01)

(58) Field of Classification Search
CPC . C12N 9/16; C12N 15/75; C12N 9/88; C12N 15/70; C12Y 301/06004; C12P 19/26
See application file for complete search history.

(56) References Cited

FOREIGN PATENT DOCUMENTS

| CN | 102220270 | 10/2011 |
|---|---|---|
| CN | 104710536 | 6/2015 |
| CN | 105802875 | 7/2016 |
| CN | 109913437 | 6/2019 |
| WO | 2006068146 | 6/2006 |

OTHER PUBLICATIONS

Whisstock et al. Quaterly Reviews of Biophysics, 2003, "Prediction of protein function from protein sequence and structure", 36(3): 307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10: 8-9. (Year: 2002).*
Huang et al., "Crystal Structure of Proteus vulgaris Chondroitin Sulfate ABC Lyase I at 1.9 A° Resolution", J. Mol. Biol., vol. 328, May 2003, pp. 1-12.
Huang et al., "PDB: 1HN0_A Chain A, Chondroitin ABC Lyas I", NCBI, Oct. 2012, pp. 1-8.
Tao Ke et al., "Study on the screening of chondroitinase ABC producing strain and their fermentation technology", Chinese Journal of Antibiotics, vol. 29, Issue 3, Mar. 2004, with English abstract, pp. 138-140.
Su Xin et al., "Fermentation Preparation of Chondroitinase and Its Isolation and Purification", Journal of Microbiology, vol. 25, Issue 4, Jul. 2005, with English abstract, pp. 64-67.
Ye Li et al., "Expression, purification and characterization of GAPDH-ChSase ABC I from Proteus vulgaris in *Escherichia coli*", Protein Expression and Purification, vol. 128, Aug. 2016, pp. 36-41.
"International Search Report (Form PCT/ISA/210) of PCT/CN2019/106448," dated Dec. 27, 2019, with English translation thereof, pp. 1-8.
"Written Opinion of the International Searching Authority (Form PCT/ISA/237) of PCT/CN2019/106448," dated Dec. 27, 2019, pp. 1-4.
Office Action of China Counterpart Application, with English translation thereof, dated Aug. 30, 2019, pp. 1-10.
Office Action of China Counterpart Application, with English translation thereof, dated Oct. 22, 2019, pp. 1-13.

* cited by examiner

*Primary Examiner* — Iqbal H Chowdhury
(74) *Attorney, Agent, or Firm* — JCIP Global Inc.

(57) ABSTRACT

Provided are chondrosulfatase and a use thereof, belonging to the technical field of biological engineering. Chondrosulfatase is screened and identified from the natural world, the maximum similarity between its amino acid sequence and that of the chondrosulfatase reported by NCBI being 85%; then the expression in *Escherichia coli* and *Bacillus subtilis* is optimized, achieving the high-efficiency biosynthesis of chondrosulfatase having high enzymatic activity, the maximum enzyme activity being 11976.5 U/L; furthermore, the entire process and post-processing are simpler. The invention has potentially broad value in application in the preparation of products containing low molecular-weight chondroitin sulfate in the fields of medicine, cosmetics, and biology, lays the foundation for efficient fermentation of a microbial system to produce a chondrosulfatase having high enzyme activity, and is suitable for industrialized production applications.

2 Claims, 2 Drawing Sheets
Specification includes a Sequence Listing.

CHONDROSULPHATASE AND USE THEREOF

CROSS-REFERENCE TO RELATED APPLICATION

This application is a 371 of international application of PCT application serial no. PCT/CN2019/106448, filed on Sep. 18, 2019, which claims the priority benefit of China application no. 201910264385.5, filed on Apr. 3, 2019. The entirety of each of the above mentioned patent applications is hereby incorporated by reference herein and made a part of this specification.

BACKGROUND

Technical Field

The present disclosure relates to the technical field of biological engineering, more particularly, relates to screening, identification and optimized expression of a Chondrosulphatase.

Description of Related Art

Chondrosulphatase (ChSase), a lyase that can degrade glycosaminoglycans such as chondroitin sulfate, dermatin sulfate and hyaluronic acid into unsaturated disaccharides and oligosaccharides. According to different substrates, ChSase can be divided into ChSase ABC, ChSase AC, ChSase B and ChSase C, etc. ChSase has important application in the fields of biochemistry and medicine. In basic research, ChSase can be used as a tool enzyme for quality study of chondroitin sulfate and efficient preparation of chondroitin sulfate oligosaccharides with multiple biological activities. In the field of medicine, ChSase is used as a medicinal enzyme, which can degrade the mucus in cystic fibrosis, promotes the regeneration of nerve axis, relieves the symptoms of lumbar disc herniation, anti-tumor, enhances the adhesion between chondrocytes and cartilage and other medicinal functions. ChSase is mainly derived from microorganisms, and most of them are lyase. Some microorganisms, such as *Flavobacterium* heparin, *Proteus penneri*, *Aeromonas sobria*, *Proteus vulgaris* and so on, can produce chondroitin sulfate lyase. However, most of the ChSase derived from microorganisms is an intracellular enzyme with low enzyme activity. Tao Ke et al. (Study on the screening of chondroitinase ABC producing strain and their fermentation technology[J]. Chinese Journal of Antibiotics, 2004, (29)3:138-140.) reports that a strain of *Proteus penneri* is used to produce ChSase by fermentation. The process is complicated, and the enzyme activity of ChSase decreases significantly in the later stage of fermentation, and in the whole process the highest enzyme activity is only 322.17 U/L. Su Xin et al. (Study on the preparation of chondroitin sulfate lyase by fermentation and its enzyme separation and purification[J]. Journal of Microbiology, 2005, (25)4:64-67) reports that a strain of *Aeromonas sobria* is screened from fish belly. Although it has a high enzyme production capacity, it needs a purification process of one-step dialysis and four-step column chromatography, which is complicated, costly and not conducive to industrial amplification. Besides fermentation, Li et al. (Expression, purification and characterization of GAPDH-ChSase ABC I from *Proteus vulgaris* in *Escherichia coli*[J]. Protein Expression and Purification, 2016, (128):36-41.) also reports that ChSase derived from *Proteus* is heterologously expressed in *E. coli*. In order to increase the expression of ChSase, glyceraldehyde-3-phosphate dehydrogenase is co-expressed, however the enzyme activity after purification is reduced by 3.1 times, so it's not conducive to industrial amplification. At present, there is no domestic product supply, almost all rely on import, and the price is very expensive, which limits the application of ChSase in the preparation of low molecular weight chondroitin sulfate and medicine. Therefore, it is of great significance to screen ChSase with high enzyme activity.

SUMMARY

The invention screens and identifies a ChSase by collecting soil samples, sewage or sludge from coastal areas, river banks, farmers' markets, slaughterhouses and dining halls. Extract suitable amount of soil samples with physiological saline, after enrichment culture, gradient dilution and spread it on the screening plate. Compare and select the colony with the largest ratio of transparent circle to strain diameter, and inoculate the colony into the liquid fermentation medium for culture. The genome of the flora is extracted for metagenomic sequencing, and the sequence with the highest possibility of ChSase is analyzed and screened. Then the sequence is artificially synthesized and further identified and optimized for expression in *E. coli* and *B. subtilis*, the expression vector is the plasmid pBRSFDuet-1, pHT01, pHT43-His, pMA5 or pWB980. The invention screens and identifies a ChSase from the nature, the highest similarity between the amino acid sequence of the ChSase and the known ChSase reported by NCBI (National Center of Biotechnology Information) is 85%. An expression of the ChSase is optimized in *Escherichia coli* and *Bacillus subtilis*, and the high-efficiency biosynthesis of high activity ChSase with the highest enzyme activity of 11976.5 U/L is achieved.

In one embodiment, the ChSase is screened and identified from soil samples, sewage or sludge from coastal areas, river banks, farmers' markets, slaughterhouses and dining halls, the highest similarity between its amino acid sequence and the ChSase reported by NCBI is 85%.

In one embodiment, the ChSase is optimally expressed in the engineered strain of *Escherichia coli* or *Bacillus subtilis*, including *E. coli* MG1655, *E. coli* DH5α, *E. coli* W3110, *E. coli* BL21, *B. subtilis* 168, *B. subtilis* WB600, *B. subtilis* WB800 and other hosts.

In one embodiment, the engineer strain is further preferred to be B. *Subtilis*, because the strain has high safety and wide range of applications.

In one embodiment, an expression vector of a ChSase gene is a plasmid of pBRSFDuet-1 or pHT01.

In one embodiment, the optimized expression of the ChSase gene included codon optimization, ribosomal binding site (RBS) optimization, promoter optimization and so on.

In one embodiment, the components of a fermentation medium are: yeast powder is 12-18 g/L, glucose is 32-48 g/L, potassium sulfate is 3.2-4.8 g/L, magnesium sulfate is 1.8-2.2 g/L, phosphate buffer is 40-60 mM, $FeCl_2 \cdot 6H_2O$ is 10.8-16.2 mg/L; $MnCl_2 \cdot 4H_2O$ is 0.8-1.2 mg/L; $ZnCl_2$ is 1.36-2.04 mg/L; $CuCl_2 \cdot 2H_2O$ is 0.344-0.516 mg/L; and pH 5-9.

In one embodiment, a fermentation method is to inoculate a recombinant strain into a fermentation medium and ferment at 30-40° C. for 20-80 h.

In one embodiment, a determination method of an enzyme activity of the ChSase includes: sonicating the fermentation broth to disrupt the cells, and the supernatant is harvested as crude enzyme by centrifugation at 12000 rpm at 4° C. for 20 min. The crude enzyme solution is purified by MBP column which eluted with 10 mM maltose. 40 μL of diluted enzyme solution is added to 960 μL of substrate solution (2 g/L of C4S is dissolved in 20 mM Tris-HCl). The initial reaction rate within 1 min is determined by kinetic-based enzyme activity determination method. Definition of the enzyme activity: the amount of enzyme required to consume 1 micromole of substrate per unit time is defined as one unit of enzyme activity.

The invention also provides a use of the ChSase in a preparation of products containing low molecular weight chondroitin sulfate in the fields of medicine, cosmetics and biology.

The beneficial effects of the invention relative to the prior art are as follows: the invention screens and identifies a ChSase from the nature, the highest similarity between its amino acid sequence and the ChSase reported by NCBI is 85%, then optimally expressed in E. coli and B. subtilis. The expression vector is the plasmid pBRSFDuet-1, pHT01, pHT43-His, pMA5 or pWB980, the efficient biosynthesis of ChSase with high enzyme activity is realized, and the highest enzyme activity is 11976.5 U/L. The whole process and post-treatment are simplified. The invention has potential and wide application value in the preparation of products containing low molecular weight chondroitin sulfate in the fields of medicine, cosmetics and biology.

DESCRIPTION OF THE EMBODIMENTS

Figure 1:
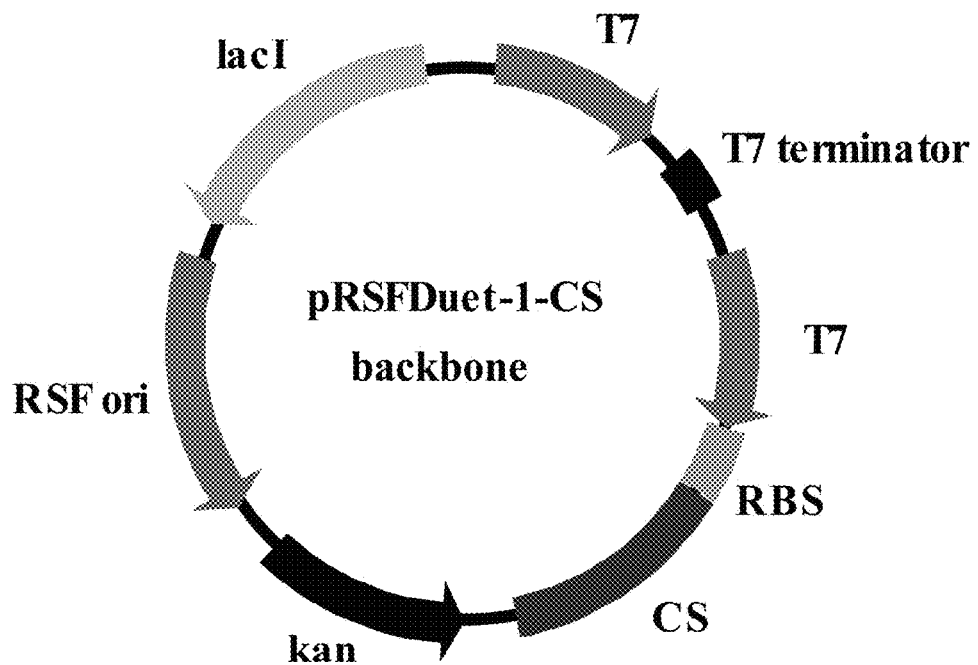
FIG. 1 shows the schematic diagram of the construction of vector for optimized expression of ChSase in E. coli.

Amino acid sequence information involved in the examples:
SEQ ID No. 1 is the amino acid sequence of a novel ChSase screened and identified from the nature of the invention.

Example 1: Screening and Identification of ChSase

Collected soil samples, sewage or sludge from coastal areas, river banks, farmers' markets, slaughterhouses and dining halls. Extracted suitable amount of soil samples with physiological saline. The enrichment cultured samples were gradient diluted and spreaded on the screening plate, then cultured at 37° C. for 3 days. The colonies with transparent circles were selected for secondary screening. The selected culture medium (g/L) was: chondroitin sulfate 4.5, ammonium chloride 2.5, sodium chloride 0.95, magnesium sulfate 1.0, dipotassium hydrogen phosphate 1.0, agar 20.0, bovine serum albumin 5.0, pH 7.0. Compared and selected the colony with the largest ratio of transparent circle to strain diameter in the re-screening plate, and inoculated the colony into the liquid fermentation medium for culture. The genome of the flora was extracted for metagenomic sequencing, and the sequence with the highest possibility of ChSase was analyzed and screened. The amino acid sequence with the highest probability of ChSase was compared with the ChSase reported by NCBI. The final result was that the highest similarity between this enzyme and the ChSase reported by NCBI was 85%. The sequence was artificially synthesized and expressed in E. coli and B. subtilis, and the results of further identification proved the enzyme was ChSase.

Example 2: Optimized Expression of ChSase in E. coli and B. subtilis

Construction of Expression System:
The fragment CS DNA was amplified by PCR with the primer CS(pBRSF)-F/CS(pBRSF)-R which used artificially synthesized CS DNA as the template. Recombinant plasmid pBRSFDuet-1-CS was constructed by splicing the CS DNA PCR product and skeleton plasmid pBRSFDuet-1 which used the primer pBRSF-F/pBRSF-R.

The fragment CS DNA was amplified by PCR with the primer CS(pHT)-F/CS(pHT)-R which used artificially synthesized CS DNA as the template. Recombinant plasmid pHT01-CS was constructed by splicing the CS DNA PCR product and skeleton plasmid pHT01 which used the primer pHT01-F/pHT01-R.

Construction of Recombinant Bacteria:
The recombinant plasmid pBRSFDuet-1-CS was transferred into E. coli MG1655, E. coli DH5α, E. coli W3110, and E. coli BL21 to construct the recombinant strain CSmg, CSdh, CSw300, and CSbl, respectively.

The recombinant plasmid pHT01-CS was transferred into B. subtilis 168, B. subtilis WB600, and B. subtilis WB800 to construct the recombinant strain CS168, CS600, and CS800, respectively.

Figure 2:
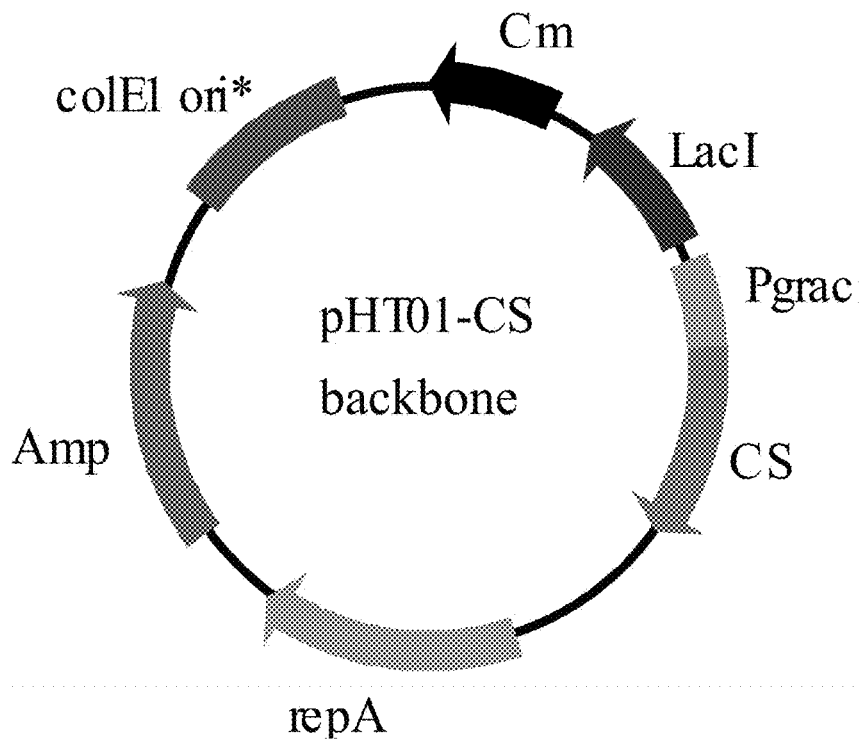
FIG. 2 shows the schematic diagram of the construction of vector for optimized expression of ChSase in B. subtilis.

The construction of E. coli vector optimized for ChSase expression is shown in FIG. 1; the construction of B. subtilis vector optimized for ChSase expression is shown in FIG. 2.

The primer information (5'-3') is as follows:

| | |
|---|---|
| pBRSF-F | AAGCTTTCGCCGTTGCCCTAACATATGGCAGATCTCA ATTGGATATCGGCCGG |
| pBRSF-R | GGTACCCATGTGTACATTCCTCTCTTTATATCTCCTT CTTATACTTAACTAATATACT |
| CS(pBRSF)-F | TAAGTATAAGAAGGAGATATAAAGAGAGGAATGTACA CATGGGTACCTCTAATCCTGCC |
| CS(pBRSF)-R | CCGGCCGATATCCAATTGAGATCTGCCATATGTTAGG GCAACGGCGAAAGCTT |
| pHT01-F | AAGCTTTCGCCGTTGCCCTAAGGATCCTCTAGAGTCG ACGTCCCCGGGGCAG |
| pHT01-R | TACCCATGTGTACATTCCTCTCTTAATTGGGAATTGT TATCCGCTCACAATTCCACAAT |
| CS(pHT)-F | AGCGGATAACAATTCCCAATTAAGAGAGGAATGTACA CATGGGTACCTCTAATCCTGCC |
| CS(pHT)-R | CTGCCCCGGGGACGTCGACTCTAGAGGATCCTTAGGG CAACGGCGAAAGCTT |

Figure 3:
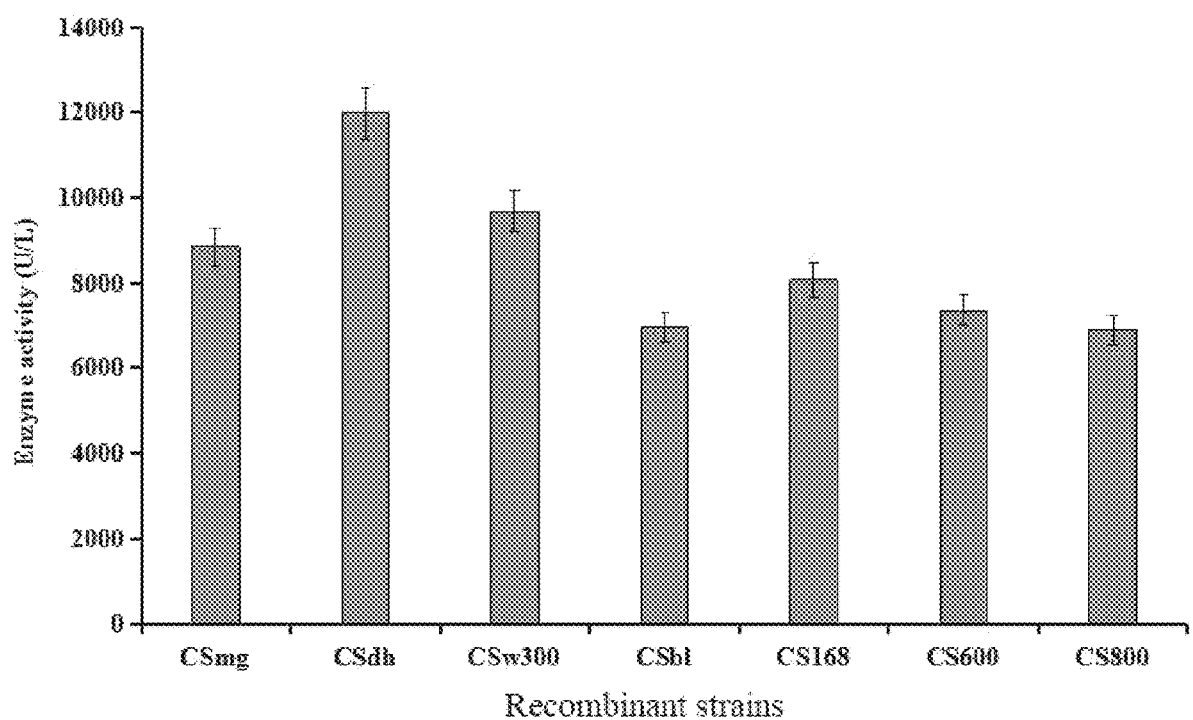
FIG. 3 shows the enzyme activity of optimized expression of ChSase in E. coli and B. subtilis cultured in shake flask for 50 h.

Monoclone of seven recombinant strains and the control strains (pBRSFDuet-1 empty plasmid and pHT01 empty plasmid were transformed by E. coli and B. subtilis, respectively) were inoculated into 5 mL LB culture containing appropriate antibiotics (the final concentration of 50 μg/mL kanamycin for E. coli and the final concentration of 25 μg/mL chloramphenicol for B. subtilis). The seed inoculum was cultured at 37° C. at 200 rpm for 10 h, and transferred to a 250 mL flask with a liquid volume of 25 mL according to the inoculation amount of 10%, and the medium was the fermentation medium. 1.5 mmol/L IPTG and appropriate antibiotics (the final concentration of 50 μg/mL kanamycin for *E. coli* and the final concentration of 25 μg/mL chloramphenicol for *B. subtilis*) were added as required. The cultures were incubated at 37° C. and 220 rpm. After an incubation time of 50 h, the enzyme activity was determined. The method of the ChSases enzyme activity was as follows: sonicating the fermentation broth to disrupt the cells, and the supernatant was harvested as crude enzyme by centrifugation at 12000 rpm and 4° C. for 20 min. The crude enzyme solution was purified by MBP column and eluted with 10 mM maltose. 40 μL of diluted enzyme solution was added to 960 μL of substrate solution (2 g/L of C4S dissolved in 20 mM Tris-HCl). The initial reaction rate within 1 min was determined by kinetic-based enzyme activity determination method. Definition of the enzyme activity: the amount of enzyme required to consume 1 micromole of substrate per unit time is defined as one unit of enzyme activity. The results of enzyme activity in FIG. 3 showed that all of the recombinant strains could realize the high-efficiency biosynthesis of high activity ChSase, and the highest ChSase activity was obtained from CSdh as 11976.5 U/L.

Although the present invention has been disclosed as above with preferred embodiments, it is not intended to limit the present invention. Anyone familiar with this technology can make various changes and modifications without departing from the spirit and scope of the present invention. Therefore, the protection scope of the present invention should be defined by the claims.

What is claimed is:

1. A chondrosulphatase, comprising the amino acid sequence which is shown in SEQ ID No. 1, wherein the chondrosulphatase is screened and identified from soil samples, sewage or sludge in coastal areas, river banks, farmers' markets, slaughterhouses and dining halls, a highest similarity between the amino acid sequence of the chondrosulphatase and known chondrosulphatase is 90%, and an expression of the chondrosulphatase is optimized in engineering strain *Escherichia coli* or *Bacillus subtilis*.

2. A method of using the chondrosulphatase according to claim 1 in a preparation of products containing low molecular weight chondroitin sulphate in fields of medicine, cosmetics and biology.

* * * * *

SEQUENCE LISTING

```
<160> NUMBER OF SEQ ID NOS: 9

<210> SEQ ID NO 1
<211> LENGTH: 998
<212> TYPE: PRT
<213> ORGANISM: Unknown
<220> FEATURE:
<223> OTHER INFORMATION: Microbial consortium, obtained by metagenome
      sequencing

<400> SEQUENCE: 1

Met Ala Thr Ser Asn Pro Ala Tyr Asp Ala Lys Asn Leu Leu Gln Ser
1               5                   10                  15

Glu Ile Tyr His Phe Ala Gln Asn Asn Pro Leu Ala Asp Phe Ser Ala
            20                  25                  30

Ser Lys Asn Ser Ile Leu Thr Leu Ser Asp Lys Arg Ser Ile Met Gly
        35                  40                  45

Asn Gln Ser Leu Leu Trp Lys Trp Gln Arg Gly Ser Ser Phe Thr Leu
    50                  55                  60

His Arg Lys Ile Leu Val Pro Thr Asp Lys Glu Ala Ser Lys Ala Trp
65                  70                  75                  80

Gly Arg Ser Ser Thr Pro Val Phe Ser Phe Trp Leu Tyr Asn Glu Lys
                85                  90                  95

Pro Ile Asp Gly Tyr Leu Thr Ile Asp Phe Gly Glu Lys Leu Ile Ser
            100                 105                 110

Thr Ser Glu Ala Gln Ala Gly Phe Lys Val Lys Leu Asp Phe Thr Gly
        115                 120                 125

Trp Arg Ala Val Gly Val Ser Leu Asn Met Asp Leu Glu Asn Lys Gln
    130                 135                 140

Glu Leu Thr Asn Ala Thr Asn Thr Ser Ser Asp Gly Thr Gln Asp Ser
145                 150                 155                 160

Ile Gly Arg Ser Leu Gly Ala Lys Val Asp Ser Ile Arg Phe Lys Ala
                165                 170                 175

Pro Ser Asn Val Ser Gln Gly Glu Ile Tyr Ile Asp Arg Ile Met Phe
            180                 185                 190

Ser Val Asp Asp Ala Arg Tyr Gln Trp Ala Asp Tyr Gln Val Lys Leu
        195                 200                 205

Arg Leu Ser Glu Pro Glu Leu Asn Phe His Thr Val Thr Pro Gln Ile
    210                 215                 220

Pro Val Thr Pro Glu Asn Ile Ala Ser Ile Asp Leu Leu Arg Gln Arg
225                 230                 235                 240

Leu Ile Asn Glu Phe Val Gly Ala Glu Lys Asp Thr Asn Thr Ala Ile
```

-continued

```
                245                 250                 255
Gln Ile Asn Val Gln Lys Leu Ile Gln Glu Tyr Glu Ala Leu Asn Ile
            260                 265                 270
Glu Leu Thr Ala Asn Gly Ala Thr Gln Gly Arg His Ile Leu Thr Glu
            275                 280                 285
Lys Gln Val Ile Leu Tyr Gln Pro Glu Asn Leu Asn Ser Gln Glu Lys
            290                 295                 300
Gln Leu Phe Glu Asn Tyr Val Ile Leu Gly Asn Tyr Thr Thr Leu Met
305                 310                 315                 320
Phe Asn Ile Ser Arg Ala Tyr Val Leu Gln Lys Glu Pro Thr Gln Lys
                325                 330                 335
Ala Gln Leu Lys Gln Met Tyr Ile Leu Met Thr Lys His Ile Leu Asp
            340                 345                 350
Gln Gly Phe Val Lys Ser Gly Ala Leu Val Leu Thr His Lys Trp Gly
            355                 360                 365
Tyr Ser Ser Arg Tyr Trp Tyr Ile Ser Thr Leu Thr Met Ser Asp Ala
            370                 375                 380
Leu Lys Glu Ala Asn Leu Gln Thr Gln Val Tyr Asp Ser Leu Leu Trp
385                 390                 395                 400
Tyr Ser Arg Glu Phe Lys Ala Ser Phe Asp Met Lys Val Ser Ala Asp
                405                 410                 415
Ser Ala Asp Leu Asp Tyr Phe Asn Thr Leu Ser Arg Gln His Leu Ala
            420                 425                 430
Leu Thr Leu Ile Glu Pro Asp Asp Gln Lys Arg Ile Asn Leu Val Asn
            435                 440                 445
Thr Phe Ser His Tyr Ile Thr Ala Gly Leu Thr Gln Val Pro Pro Gly
            450                 455                 460
Ala Arg Asp Ala Leu Arg Pro Asp Gly Thr Ala Trp Arg His Glu Gly
465                 470                 475                 480
Asn Tyr Pro Gly Tyr Ala Phe Pro Ala Phe Lys Asp Ala Ser Gln Leu
                485                 490                 495
Ile Tyr Leu Leu Lys Asp Thr Pro Phe Ser Val Ala Gln Ser Gly Trp
            500                 505                 510
Asn Asn Leu Lys Arg Ala Met Val Ala Ser Trp Ile Tyr Ser Asn Pro
            515                 520                 525
Gln Val Gly Leu Pro Leu Ala Gly Lys His Pro Phe Asn Ser Pro Leu
            530                 535                 540
Ser Lys Ser Val Ala Gln Gly Tyr Gln Trp Leu Ala Met Ser Ala Lys
545                 550                 555                 560
Ala Ser Pro Asp Lys Thr Leu Ser Ala Ile Tyr Leu Ala Leu Ser Asp
                565                 570                 575
Lys Thr Gln Asn Gln Ser Thr Ala Leu Phe Gly Glu Thr Ile Thr Pro
            580                 585                 590
Ala Ser Leu Pro Gln Gly Phe Tyr Ala Phe Asn Gly Ala Ala Phe Gly
            595                 600                 605
Ile His Arg Trp Gln Asp Lys Met Val Thr Leu Lys Ala Tyr Asn Thr
            610                 615                 620
Asn Trp Val Ala Ser Glu Ile Tyr Asn Lys Asp Met Arg Tyr Gly Arg
625                 630                 635                 640
Tyr Gln Ser His Gly Val Ala Gln Ile Val Ser Asn Gly Ser Gln Leu
                645                 650                 655
Ser Gln Gly Tyr Gln Gln Glu Gly Trp Glu Trp Asn Arg Met Glu Gly
            660                 665                 670
```

Ala Thr Ile Leu His Leu Pro Leu Lys Asp Ile Glu Ser Pro Lys Pro
            675                 680                 685

His Thr Ile Asn Gln Arg Gly Glu Arg Gly Phe Ser Gly Thr Ala Ser
            690                 695                 700

Leu Glu Ala Gln Tyr Gly Met Asn Ser Phe Asn Ile Leu Tyr Pro Ala
705                 710                 715                 720

Asn Leu Glu Arg Phe Asp Pro Asn Phe Thr Ala Lys Arg Ser Val Leu
                725                 730                 735

Ser Ala Asp Asn His Leu Ile Phe Ile Ser Gly Asn Ile Met Ala Ser
            740                 745                 750

Asp Lys Lys Asn Pro Val Glu Thr Thr Ile Phe Gln His Ala Ile Thr
            755                 760                 765

Pro Thr Ile Asn Leu Thr Trp Ile Asn Gly Gln Lys Leu Glu Asn Met
770                 775                 780

Pro Tyr Gln Thr Leu Ile Gln Asp Gly Glu Trp Leu Ile Asp Ser Met
785                 790                 795                 800

Gly Asn Ala Tyr Ile Leu Leu Gln Ala Glu Lys Val Asn Ile Ser Arg
                805                 810                 815

Gln His Gln Val Ser Ala Gln Asn Arg Asn Arg Gln Pro Thr Gln Ala
            820                 825                 830

Asn Phe Ala Ser Ala Trp Ile Asp His Ser Thr Lys Pro Lys Asp Ala
            835                 840                 845

Ser Tyr Glu Tyr Met Val Phe Ile Asp Ala Thr Pro Glu Lys Met Gly
            850                 855                 860

Glu Met Ala Gln Lys Phe Arg Glu Asn Asn Gly Leu Tyr Gln Val Leu
865                 870                 875                 880

Arg Lys Asp Lys Asp Val His Ile Ile Leu Asp Lys Leu Ser Asn Val
                885                 890                 895

Thr Gly Tyr Ala Phe Tyr Gln Pro Ala Ser Ile Glu Asp Lys Trp Ile
            900                 905                 910

Lys Arg Val Asn Lys Pro Ala Ile Val Met Thr His Lys Gln Arg Asp
            915                 920                 925

Thr Ile Leu Val Ala Ser Val Thr Pro Asp Leu Asn Met Thr Arg Gln
            930                 935                 940

Lys Ala Ser Thr Pro Val Thr Ile Asn Leu Thr Leu Asn Gly Lys Trp
945                 950                 955                 960

Gln Ala Ser Asp Lys Asn Ser Glu Val Arg Tyr Gln Val Ser Gly Asp
                965                 970                 975

Asn Thr Glu Leu Thr Phe Thr Ser Tyr Phe Gly Ile Pro Gln Glu Ile
            980                 985                 990

Lys Leu Ser Pro Leu Pro
        995

<210> SEQ ID NO 2
<211> LENGTH: 53
<212> TYPE: DNA
<213> ORGANISM: Artificial Sequence
<220> FEATURE:
<223> OTHER INFORMATION: Synthetic

<400> SEQUENCE: 2
aagctttcgc cgttgcccta acatatggca gatctcaatt ggatatcggc cgg         53

<210> SEQ ID NO 3
<211> LENGTH: 58

```
<212> TYPE: DNA
<213> ORGANISM: Artificial Sequence
<220> FEATURE:
<223> OTHER INFORMATION: Synthetic

<400> SEQUENCE: 3
ggtacccatg tgtacattcc tctctttata tctccttctt atacttaact aatatact        58

<210> SEQ ID NO 4
<211> LENGTH: 59
<212> TYPE: DNA
<213> ORGANISM: Artificial Sequence
<220> FEATURE:
<223> OTHER INFORMATION: Synthetic

<400> SEQUENCE: 4
taagtataag aaggagatat aaagagagga atgtacacat gggtacctct aatcctgcc       59

<210> SEQ ID NO 5
<211> LENGTH: 53
<212> TYPE: DNA
<213> ORGANISM: Artificial Sequence
<220> FEATURE:
<223> OTHER INFORMATION: Synthetic

<400> SEQUENCE: 5
ccggccgata tccaattgag atctgccata tgttagggca acggcgaaag ctt             53

<210> SEQ ID NO 6
<211> LENGTH: 52
<212> TYPE: DNA
<213> ORGANISM: Artificial Sequence
<220> FEATURE:
<223> OTHER INFORMATION: Synthetic

<400> SEQUENCE: 6
aagctttcgc cgttgcccta aggatcctct agagtcgacg tccccggggc ag              52

<210> SEQ ID NO 7
<211> LENGTH: 59
<212> TYPE: DNA
<213> ORGANISM: Artificial Sequence
<220> FEATURE:
<223> OTHER INFORMATION: Synthetic

<400> SEQUENCE: 7
tacccatgtg tacattcctc tcttaattgg gaattgttat ccgctcacaa ttccacaat       59

<210> SEQ ID NO 8
<211> LENGTH: 59
<212> TYPE: DNA
<213> ORGANISM: Artificial Sequence
<220> FEATURE:
<223> OTHER INFORMATION: Synthetic

<400> SEQUENCE: 8
agcggataac aattcccaat taagagagga atgtacacat gggtacctct aatcctgcc       59

<210> SEQ ID NO 9
<211> LENGTH: 52
<212> TYPE: DNA
```

-continued

```
<213> ORGANISM: Artificial Sequence
<220> FEATURE:
<223> OTHER INFORMATION: Synthetic

<400> SEQUENCE: 9
ctgccccggg gacgtcgact ctagaggatc cttagggcaa cggcgaaagc tt        52
```